(12) United States Patent
Peterson et al.

(10) Patent No.: US 6,251,279 B1
(45) Date of Patent: Jun. 26, 2001

(54) HEAT DISINFECTION OF A WATER SUPPLY

(75) Inventors: Michael J. Peterson, Nashville; Richard M. Russell, Brentwood, both of TN (US)

(73) Assignee: Dialysis Systems, Inc., Nashville, TN (US)

( * ) Notice: Subject to any disclaimer, the term of this patent is extended or adjusted under 35 U.S.C. 154(b) by 0 days.

(21) Appl. No.: 09/458,140

(22) Filed: Dec. 9, 1999

(51) Int. Cl.$^7$ .................................................. B01D 61/24
(52) U.S. Cl. ........................... 210/636; 210/97; 210/138; 210/321.69; 210/646; 210/764; 134/22.11; 422/28
(58) Field of Search ............................. 210/86, 104, 139, 210/175, 257.1, 321.69, 636, 646, 744, 764, 774, 138, 97; 134/22.1, 22.11, 22.12, 22.13, 22.14, 104.1, 166 C, 168 C; 422/28, 105, 116; 138/137; 604/4.01

(56) References Cited

U.S. PATENT DOCUMENTS

| | | | |
|---|---|---|---|
| 4,444,597 | 4/1984 | Gortz et al. | 210/646 |
| 4,942,630 | 7/1990 | Kantor et al. | |
| 5,139,675 | 8/1992 | Arnold et al. | 210/636 |
| 5,147,613 * | 9/1992 | Heilmann et al. | 210/321.69 |
| 5,158,441 | 10/1992 | Aid et al. | |
| 5,244,579 | 9/1993 | Horner et al. | 210/636 |
| 5,254,250 | 10/1993 | Rolchigo et al. | |
| 5,256,371 | 10/1993 | Pippert. | |
| 5,336,165 | 8/1994 | Twardowski | 210/636 |
| 5,401,421 | 3/1995 | Blum | 210/646 |
| 5,433,843 | 7/1995 | Calabrese. | |
| 5,480,565 | 1/1996 | Levin et al. | 210/764 |
| 5,484,397 | 1/1996 | Twardowski | 210/636 |
| 5,494,573 | 2/1996 | Schoenmeyr et al. | |
| 5,543,040 | 8/1996 | Fite, Jr. et al. | |
| 5,562,127 * | 10/1996 | Fanselow et al. | 138/178 |
| 5,582,600 | 12/1996 | Loh. | |
| 5,589,070 | 12/1996 | Maltais et al. | |
| 5,591,344 | 1/1997 | Kenley et al. | 210/636 |
| 5,601,421 | 2/1997 | Lee. | |
| 5,624,551 | 4/1997 | Baumann et al. | |
| 5,759,489 * | 6/1998 | Miura et al. | 210/636 |
| 5,948,247 * | 9/1999 | Gillerfalk et al. | 210/636 |
| 5,972,223 * | 10/1999 | Jonsson et al. | 210/646 |

OTHER PUBLICATIONS

Appendix B to ANSI/AAMI ST35–1991, copyright 1996 by the Association for the Advancement of Medical Instrumentation.

Exhibit "A" is a two page document prepared by Applicants and entitled Heat Disinfectable Permeate Loop, Nashville, TN VA, undated.

Exhibit A is a brochure of Gambro entitled Water for Dialysis.

Exhibit B is a 510 K Summary for this same machine that was described in Exhibit A. Exhibit B is dated Sep. 23, 1998.

Exhibit C is another brochure entitled "The Gambro CWP100WRO H". This brochure is dated on its last page as year 2000, thus the brochure Exhibit C does not appear in itself to be prior art. It does, however, appear to describe the same system as described in Exhibits A and B and is thus disclosed in the interest of complete disclosure.

* cited by examiner

Primary Examiner—Joseph W. Drodge
(74) Attorney, Agent, or Firm—Waddey & Patterson; Lucian Wayne Beavers

(57) ABSTRACT

A system is provided for the heat disinfection of a fluid supply system for a dialysis machine. The system is provided with plastic conduits constructed of a material suitable for heat disinfection, preferably cross linked polyethylene conduit. A source of hot water is provided, and the hot water is flowed through the plastic conduit for sufficient time and at a sufficient temperature to disinfect the plastic conduit. This system uses a heat exchanger that utilizes fluid provided from a boiler to heat the water. The fluid supply system may employ bicarbonate fluid.

40 Claims, 3 Drawing Sheets

HEAT DISINFECTION OF A WATER SUPPLY

BACKGROUND OF THE INVENTION

1. Field of the Invention

The present invention relates generally to systems for heat disinfection of fluid supply systems for dialysis clinics.

2. Description of the Prior Art

Traditionally, the fluid supply systems to dialysis clinics have been constructed of metal piping and/or PVC plastic piping which has been permanently installed in the walls and other cavities of the building in which the dialysis clinic is located. Often there are long distances of hundreds of feet between the ultrapure water and dialysate fluids sources utilized for the clinic, and the dialysis machines themselves, thus resulting in very long lengths of such piping in the supply system.

The fluid supply systems of dialysis clinics must be frequently monitored for the presence of bacteria and endotoxins, and periodically the fluid supply systems must be disinfected.

Traditional fluid supply systems for dialysis clinics have been disinfected by chemical means. The PVC plastic piping which has traditionally utilized in such systems cannot withstand the temperatures involved in heat disinfection with hot water.

To the extent that heat disinfection has been tried in prior art systems, those systems have relied on extremely expensive plastic materials such as polytetrafluoroethylene (Teflon®) piping which is cost prohibitive for most applications.

The prior art has also included isolated equipment components, such as the dialysis machines themselves, which have sometimes been fabricated from materials suitable for heat disinfection. Such a component is shown, for example, in U.S. Pat. No. 5,591,344 to Kenley et al.

What the prior art has not provided, is a complete system including extensive piping runs constructed from affordable materials in combination with suitable processes for heat disinfection of such a system in a reliable and economical manner.

SUMMARY OF THE INVENTION

The present invention provides just such an improved system. A method of heat disinfecting a fluid supply system for a dialysis machine is provided which includes the steps of providing the fluid supply system with a cross linked polyethylene and/or polypropylene plastic conduit; providing a source of hot water; and flowing the hot water through the plastic conduit for a sufficient time and at a sufficient temperature to disinfect the plastic conduit.

The cross linked polyethylene plastic conduit can be provided in very long continuous lengths of flexible conduit which can be unrolled from a coil of such conduit in lengths in excess of 100 feet. Various straight sections of conduit and fittings to be utilized with such a system are preferably constructed from polypropylene plastic. The polypropylene material is suitable from both the economic standpoint and its compatibility with the heat disinfection processes.

In one embodiment, the heat disinfection process includes the application of hot water at a temperature of at least 190° F. and for a time of from 15 minutes to one hour. If the temperature is increased to at least 220° F., the time can be reduced to no more than half hour.

Depending upon the construction of the system, it may be necessary to bypass certain heat sensitive components of the system. For example, conventional reverse osmosis units may not be suitable for heat disinfection and thus, may need to be bypassed.

The heated water for use in the disinfection process is preferably provided by passing ultrapure water through one side of a heat exchanger, while passing a second fluid from a low pressure boiler through the other side of the heat exchanger to heat the ultrapure water.

Modified techniques are provided for use in systems utilizing a centralized bicarbonate mixing devices. When such a device is present, the bicarbonate solution must first be flushed from the system.

It is therefore, an object of the present invention to provide improved methods and apparatus for disinfection of a fluid supply system for a dialysis clinic.

Another object of the present invention is the provision of fluid supply systems utilizing cross linked polyethylene plastic conduit which can be heat disinfected.

Still another object of the present invention is the provision of systems including a heat exchanger for heating ultrapure water via heat exchange with a fluid from a low pressure boiler.

Still another object of the present invention is the provision of procedures for heat disinfection wherein heat sensitive components of a system may be bypassed.

Still another object of the present invention is the provision of procedures for heat disinfection of a fluid supply system including a centralized bicarbonate mixing device.

Other and further objects, features and advantages of the present invention will be readily apparent to those skilled in the art upon a reading of the following disclosure when taken in conjunction with the accompanying drawings.

DETAILED DESCRIPTION OF THE PREFERRED EMBODIMENTS

Figure 1:
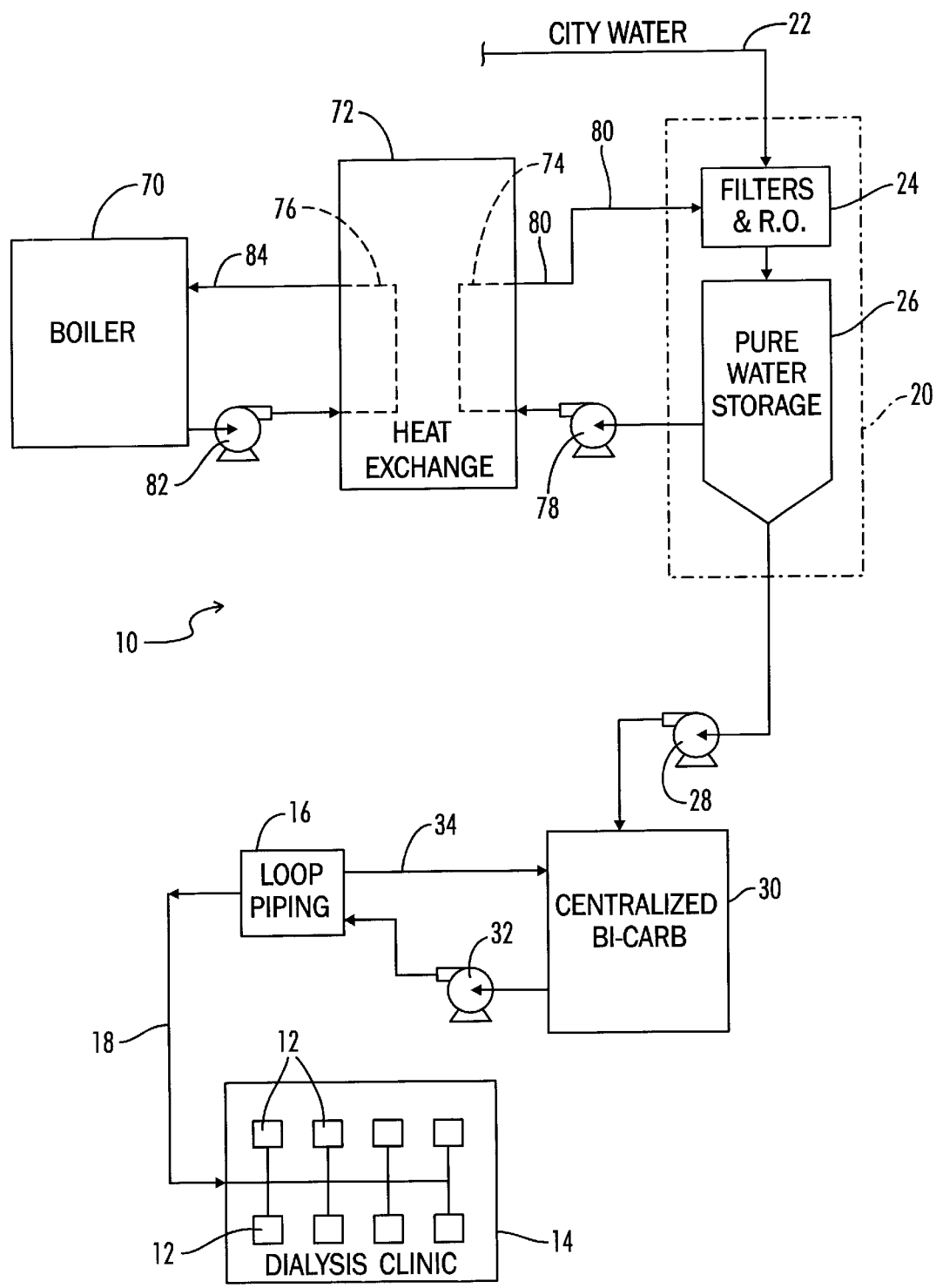
FIG. 1 is a schematic illustration of the fluid supply system for a dialysis clinic, utilizing the heat disinfection system of the present invention.

Referring now to the drawings, and particularly to FIG. 1, a fluid supply system for a dialysis clinic incorporating the present invention is shown and generally designated by the numeral 10. The system 10 provides ultrapure water and various additives to the individual dialysis machines 12 of a dialysis clinic 14. This ultrapure water plus additives is often referred to as dialysate.

The dialysate flows through one side of the dialysis machines 12 and is used to carry away contaminants drawn from the patient's blood. The ultrapure water is provided to each of the dialysis machines by flowing the same through a continuous loop which runs past each of the dialysis machines. In FIG. 1, the continuous loop is schematically illustrated at 16, with the communication from that loop to the individual dialysis machines being represented schematically at 18. It will be understood that the continuous loop 16 actually runs past each of the individual dialysis machines 12, so that ultrapure water is constantly available to each machine. The water which is utilized by the individual dialysis machines is then subsequently passed to a waste water discharge (not shown).

The ultrapure water is provided by a pure water source generally designated by the numeral 20.

City water is provided by conduit 22 to the pure water source. The city water is passed through a series of filters and a reverse osmosis machine, which are collectively designated in FIG. 1 by the numeral 24. The purified water is stored in a pure water storage tank 26 from which it is subsequently pumped by a circulation pump 28 which carries it to the dialysis clinic 14.

One of the additives which must be mixed with the pure water is a dry additive powder such as sodium bicarbonate which is used to form a sodium bicarbonate solution. Depending upon the design of the clinic, this may be done individually adjacent each dialysis machine 12 or in some instances, the sodium bicarbonate solution will be provided by a centralized bicarbonate mixing system which is schematically illustrated as item 30 in FIG. 1. If a centralized bicarbonate system 30 is utilized, the pure water will be pumped by pump 28 from pure water storage 26 to the centralized bicarbonate mixing system. A second circulating pump 32 will circulate the bicarbonate solution from the centralized bicarbonate mixing system 30 to the loop piping 16. That fluid will flow in a continuous loop and will return to the centralized bicarbonate mixing system through return conduit 34.

The Ultrapure Water System

The ultrapure water system may be either a permanent system constructed in place within the building in which the dialysis clinic is located, or it may be a portable system.

A suitable portable ultrapure water system may, for example, be constructed in accordance with the teachings of our pending U.S. patent application Ser. No. 09/122,000 filed Jul. 24, 1998, entitled "PORTABLE WATER TREATMENT FACILITY", the details of which are incorporated herein by reference.

The ultrapure water system may also be a permanent system constructed in place within the building. In either event, the typical functional components of this system will include a plurality of filters and reverse osmosis machine as was previously noted as item 24 in FIG. 1.

Figure 2:
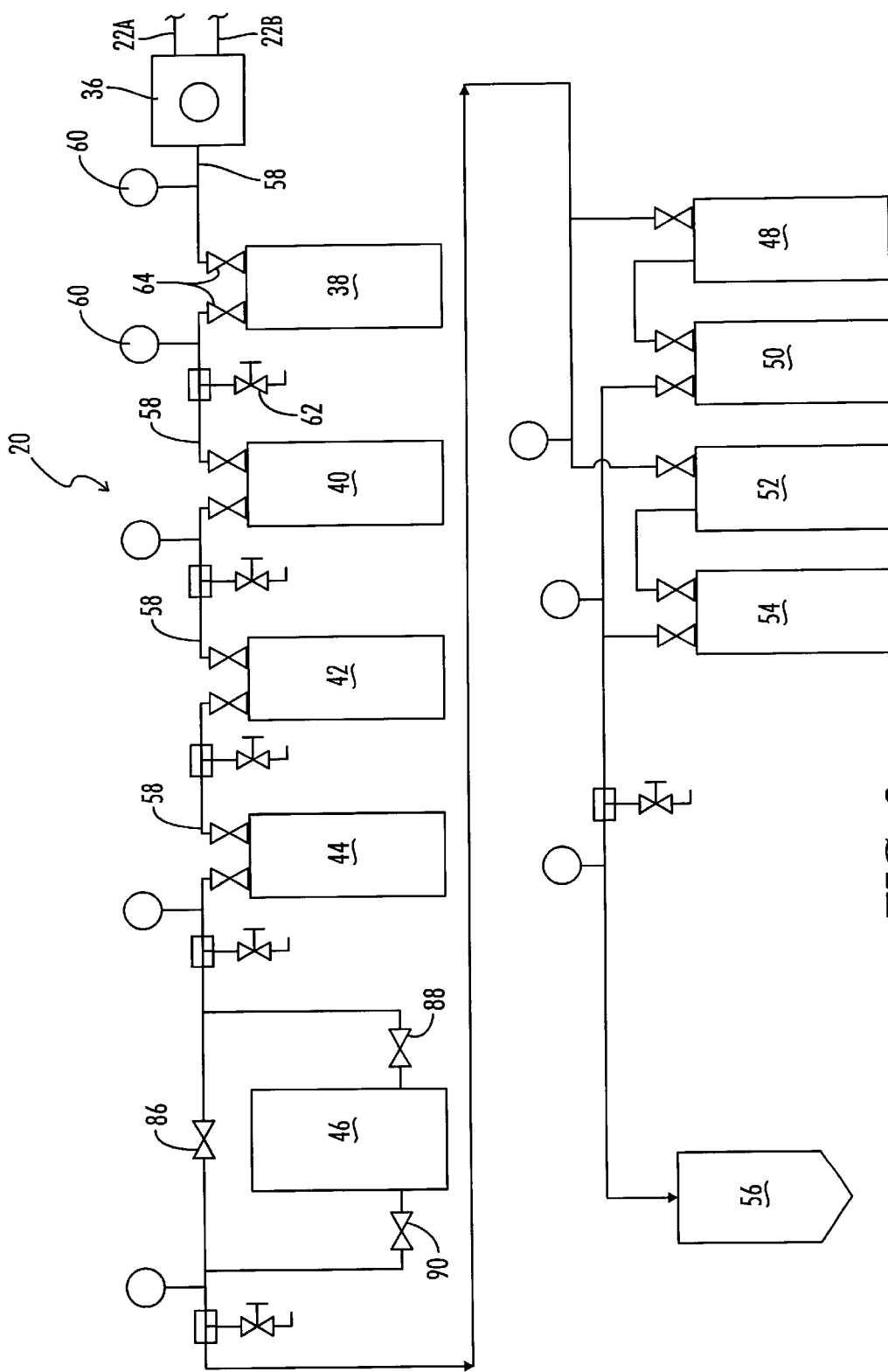
FIG. 2 is an enlarged, more detailed schematic illustration of the ultrapure water source for the dialysis clinic.

FIG. 2 is an enlarged, more detailed description of the components of the ultrapure water system 20.

Hot and cold city water supply lines 22A and 22B are connected to a tempering valve 36 which provides city water of suitable temperature to the system. Water, with or without various additives, may be generally referred to herein as aqueous fluid.

The pure water system 20 includes a plurality of filters connected in series, and one example of a typical system would include a mixed media depth filter 38 of the cartridge type, a softener 40, a first carbon tank 42, a second carbon tank 44, and a reverse osmosis unit 46. Following the reverse osmosis unit, there are two parallel sets of de-ionizing units including a first de-ionizing worker unit 48 followed by a first de-ionizing polishing unit 50 in parallel with a second de-ionizing worker unit 52 followed by a second de-ionizing polisher unit 54. Downstream of the de-ionizing units is a storage tank 56 which holds the ultrapure water. The various filters, softeners, reverse osmosis units and de-ionizing units may be generally referred to as purifying components of the pure water supply system 20.

The various purifying components are plumbed in series, that is, the water from the city water supply first flows through the mixed media filter 38, then flows through the softener 40, the flows through the first carbon tank 42, etc. The various piping conduits connecting the purifying components in the series may be collectively referred to as a pipe header 58. Other typical components of such a piping system include pressure gauges, such as 60 and sample drain valves such as 62. Also included are shut off valves, such as 64, disposed in the pipe header 58 on either side of a given purifying component.

The Centralized Bi-Carbonate Mixing Device

Various versions of centralized bicarbonate mixing systems are known to those skilled in the art. The centralized bicarbonate mixing system 30, may, however, be a system such as that disclosed in our pending U.S. Provisional Application Ser. No. 60/137,647 filed Jun. 4, 1999, entitled "CENTRALIZED BI-CARBONATE MIXING SYSTEM", the details of which are incorporated herein by reference.

The Piping System

The various piping components of the system 10 are preferably constructed from selected materials which can suitably withstand the heat disinfection processes described below.

A preferred material for certain portions of the conduit is flexible cross linked polyethylene. Other suitable materials may include polypropylene or polytetrafluoroethylene (Teflon®). Generally, the cross linked polyethylene material has been found superior for the tubing components where long seamless runs of tubing can be used because of its inherent flexibility and also due to its relatively modest price.

Another advantage of the cross linked polyethylene tubing is that it is relatively flexible and can be provided in coils of long length. Thus, when long lengths of tubing are needed perhaps to connect a remote pure water source 20 to a dialysis clinic 14 located many hundreds of feet away, long lengths of flexible cross linked polyethylene conduit may be provided by uncoiling the same from a coil of flexible conduit. Preferably, where extremely long lengths of conduit are necessary, it is provided through the use of such seamless flexible conduit.

For more modest lengths of conduit, and particularly those within the dialysis clinic 14 itself, it may be preferable to utilize pre-fabricated lengths of straight tubing in the form of modular conduit assemblies, such as those which are shown, for example, in our U.S. patent application Ser. No. 09/206,904 filed Dec. 7, 1998, now U.S. Pat. No. 6,192,197, entitled "SYSTEM FOR FLUID DELIVERY IN A DIALYSIS CLINIC", the details of which are incorporated herein by reference. These prefabricated straight lengths of tubing are preferably constructed of polypropylene which is relatively more rigid and structurally stronger than is the cross linked polyethylene.

Figure 3:
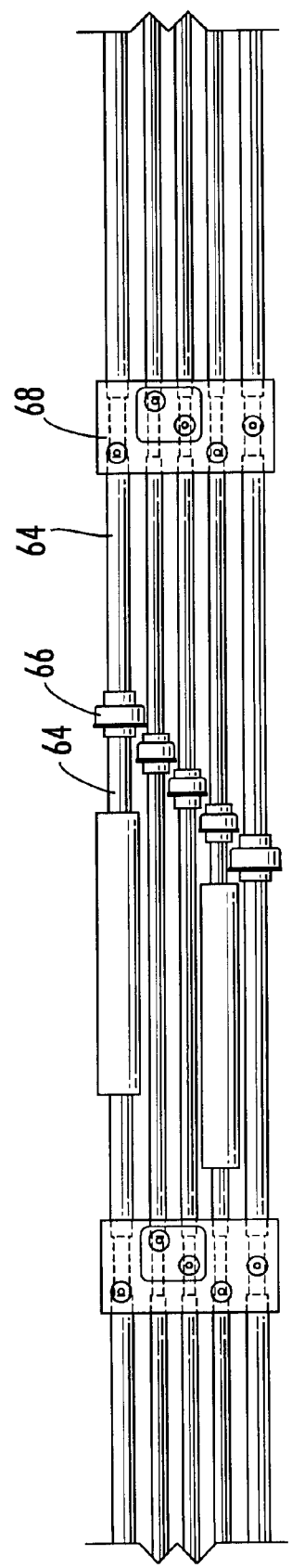
FIG. 3 is an elevation view of a segment of plastic piping, including fittings.

FIG. 3 illustrates a portion of one such modular piping assembly as disclosed in our application Ser. No. 09/206,904, now U.S. Pat. No. 6,197,197, and as is there seen, the conduit includes lengths of straight polypropylene conduit 64 which are connected by fittings such as 66 and 68. The fittings 66 and 68 are preferably formed from polypropylene material which is more readily machined in order to form such fittings.

The Heat Disinfection Apparatus and Methods

Returning now to FIG. 1, the system 10 of the present invention includes a low pressure boiler 70 and a heat exchanger 72 which as described below are utilized in conjunction with the pure water source 20 to heat the water being circulated through the system 10 at the appropriate time in order to heat disinfect the various components and conduits of the system 10.

The heat exchanger 72 is preferably a plate and frame type heat exchanger utilizing stainless steel plates. It may, for example, be a type GPX34 heat exchanger such as provided by ITT Fluid Technology Corp.

The plate and frame type exchanger is preferred for two reasons. First, it only contains a small volume of fluid and thus it reduces the total volume of fluid in the system which must be heated. The model CPX34 exchanger, for example, only contains a clear fluid volume of 0.21 gal. Second, this type of heat exchanger can raise the temperature of the lower temperature fluid to within 2° F. of that of the high temperature fluid.

The heat exchanger 72 includes a first side schematically designated by the numeral 74, which may also be referred to as a clean side 74. The heat exchanger 72 further includes a second side schematically illustrated as 76, which may also be referred to as a dirty side 76.

As will be understood by those skilled in the art, the heat exchanger 72 will pass fluid flowing through its first and second sides 74 and 76 in heat exchange relationship so as to transfer heat from the hotter fluid to the cooler fluid.

It will be further understood that other types of heat exchangers in addition to the plate and frame heat exchanger could be utilized for the heat exchanger 72.

A circulating pump 78 circulates ultrapure water from storage tank 26 through the first side 74 of heat exchanger 72, and the same returns to ultrapure water source 20 through a return conduit 80.

A second circulating pump 82 circulates hot water from the low pressure boiler 70 through the second side 76 of heat exchanger 72, and the same is returned to the boiler 70 through return conduit 84.

Heat Disinfection Methods

The methods of heat disinfecting the system 10 include providing such a fluid system 10 having conduits constructed from cross linked polyethylene conduit or other suitable plastic conduits which can withstand the heat treatment. A source of hot water is provided such as the heat exchanger 72 which heats the ultrapure water flowing through the first side 74 thereof. This heated ultrapure water is then flowed from the return conduit 84 back through the various components of the ultrapure water system 20 and then from the pure water storage tank 26 via pump 28 to the other components of system 10, such as the centralized bicarbonate unit 30, the loop piping 16, and on to the individual dialysis machines 12 themselves, if so desired.

In general, the systems and methods of the present invention may be utilized to heat disinfect any component of the system 10 which is constructed to tolerate the presence of the hot water utilized for the heat disinfection. It will be also understood that certain heat sensitive components of particular systems may need to be bypassed in order to prevent damage thereto. For example, the reverse osmosis unit 46 shown in FIG. 2, will for many systems be constructed of materials which cannot tolerate the hot water utilized for heat disinfection. In such a system, a bypass valve 86 may be utilized in conjunction with shut off valves 88 and 90 to isolate the reverse osmosis unit 46 from the hot water and to bypass the hot water past the reverse osmosis unit 46 by opening valve 86 and closing valves 88 and 90.

Other heat sensitive components of the system 10 may, in fact, include the dialysis machines 12 themselves, which may also be bypassed during the heat disinfection procedure if desired.

We have determined that the disclosed materials, such as the cross linked polyethylene and the polypropylene can be satisfactorily disinfected by flowing hot water therethrough at a temperature of at least 190° F. for a time in a range of from 15 minutes to one hour.

If the temperature is increased to at least 220° F., sufficient disinfection can typically be accomplished in no more than one-half hour.

During the heat disinfection process, the heat heated ultrapure water is circulated through the system 10 at rates comparable to those at which it is circulated during normal operation of the dialysis clinic. It will, of course, be understood that the dialysis clinic 14 will not be in operation at such time as the heat disinfection process is ongoing. The system will preferably be continuously monitored such as to provide an alarm and a status at each patient chair should the system be in heat disinfect mode, so that health care personnel will not inadvertently try to operate the dialysis machines while the system is being disinfected.

It is also significant that the heated water can be circulated through the system 10 very quickly, thus aiding in the rapid disinfection of the system. All of the various tubing components will typically only contain on the order of 10 to 25 gallons of water. The circulating pumps 28 and/or 32 will typically operate at a flow rate on the order of 20 gallons per minute. Thus, hot water can circulate through the entire system 10 in only a few minutes at most.

It will be appreciated that in typical fluid supply systems, some of the places most susceptible to the growth of micro organisms are located in components such as the pure water storage tank 26 and the centralized bicarbonate mixing device 30, and other components which may have large volumes of fluid stored therein. The use of heated water for heat disinfection will effectively heat disinfect the entire interior of such components by spraying the heated water into the top of the device and due to the presence of low pressure steam which will rise into the various niches of such components which are not, in fact, completely filled with the heated water.

It is noted that as utilized herein the term "disinfection" means the destruction of pathogenic and other micro organisms, but it does not rise to the level of "sterilization". Disinfection is a less lethal process than sterilization, since it destroys most recognized pathogenic organisms, but not necessarily all microbial forms, such as bacterial spores. Disinfection processes do not ensure the margin of safety associated with sterilization processes. This distinction between disinfection and sterilization is defined in ANSI/AAMI ST35-1991 Appendix B entitled "THERMAL DISINFECTION", copyrighted 1996 by the Association for the Advancement of Medical Instrumentation, the details of which are incorporated herein by reference.

The use of a low pressure boiler 70 as the heat source for the heat exchanger 72 is significant in that applicable safety codes allow the presence of such a low pressure boiler in a hospital or other such healthcare facility without the need for constant supervision of the boiler. Thus, via use of a low pressure boiler, heat can be provided in a safe and economical manner for the heat exchanger 72. The low pressure boiler will typically provide hot water at temperature of up to about 222° F. at a pressure of no greater than about 3 psig.

It is also important to operate the heat exchanger 72 in a manner such as to prevent contamination of the ultrapure water flowing through the first side 74 thereof. This can be accomplished by maintaining the pressure of the ultrapure water in the first side 74 of heat exchanger 72 higher than the pressure of the hot water from low pressure boiler 70 flowing through the second side 76 of heat exchanger 72, so that in the event of leaks in the heat exchanger 72, the ultrapure water in the first side 74 cannot be contaminated by the fluid in the second side 76 of the heat exchanger 72.

The heat exchanger 72, boiler 70 and associated pumps and conduits are preferably installed as a permanent part of the fluid supply system 10 so that they are readily available for use in the heat disinfection process whenever desired. For example, the operating schedule for the system 10 may be set up as to provide for weekly or other periodic heat disinfection. The same would typically be done during evening hours when use of the dialysis clinic 14 is not scheduled. The system 10 allowing easy and economic heat disinfection thereof through the use of permanently installed equipment will allow for much more frequent disinfection of the system 10 at much lower costs than is possible with conventional chemical disinfection which is typically used in traditional dialysis clinics. This will result in an overall much greater sanitation level of the system and in reduced health complications for patients utilizing the dialysis clinic. The system 10 may be provided with thermal sensing devices and timer controls to automatically carry out the heat disinfection process at an acceptable time, such as on a weekend evening.

As previously noted, the system 10 does not necessarily include a centralized bicarbonate mixing system 30, although it may. When utilizing a centralized bicarbonate mixing device 30, further modifications of the heat disinfection procedures are required. The sodium bicarbonate solution cannot be heated without detrimental effect upon the solution in the system in which it is contained, thus, when it is desired to heat disinfect a system utilizing a centralized bicarbonate mixing device 30, it is necessary to first flush the bicarbonate solution from the system. Then, ultrapure water in the source 20 without any additional additives may be circulated through the system 10, including the centralized bicarbonate device 30 to heat disinfect the same.

The present invention is particularly useful in systems which do include a centralized bicarbonate mixing device 30, because as will be understood by those skilled in the art, bicarbonate solution becomes contaminated much faster than the ultrapure water alone, and thus, all portions of the system exposed to bicarbonate solution must typically be disinfected much more often. The present heat disinfection system is much more suitable for frequent disinfection than are traditional chemical disinfection systems.

It will also be appreciated that the system 10 and particularly the pure water storage tank 26 will, in normal operation, contain a large volume of water. It is, of course, expensive to heat such large volumes of water, and it is not actually necessary when disinfecting the system 10 to have the water level in the storage tank 26 at normal operating levels. Thus, it is typically sufficient to draw down the water level in the storage tank 26 to a level above the minimum which is required to prevent cavitation in the circulation pumps 28 and 78. This will minimize the volume of water which must be heated, thus, increasing the speed at which the heat disinfection process can be accomplished, and reducing the energy costs thereof. For a typical system, the volume of water present when it is drawn down to the minimum levels to be utilized for the heat disinfection process would be on the order of 75 to 100 gallons.

When utilizing the minimum disinfection periods described above, the heated ultrapure water which is circulated through the system 10 to disinfect the same will contain the residual organic material from the various bacteria and the like which have been killed during the disinfection process, and those materials can be eliminated from the system by disposing of the heated water which has been circulated through the system 10.

Alternatively, the heat treating process can be continued for a sufficient time to actually destroy the organic materials (endotoxins) resulting from the killed bacteria, and in that case, the heated water which was utilized for the heat disinfection process can simply be allowed to cool and then be reused in the dialysis clinic. Typically, if a temperature of at least 190° F. is maintained for a time of at least six hours, it will result in such destruction of the residual organic material (endotoxins) from the bacteria as to allow reuse of the water in the dialysis clinic. It can be generally described as flowing the hot water through the system for a sufficient time and at a sufficient temperature so that substantially all endotoxins in the fluid supply system are destroyed.

Thus, it is seen that the methods and apparatus of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. A method of heat disinfecting a fluid supply system for a dialysis machine, comprising:

(a) providing the fluid supply system with a cross-linked polyethylene plastic conduit;

(b) providing a source of hot water and processing said hot water by heating said water with other fluid provided from a boiler; and (c) flowing the hot water through the plastic conduit for a sufficient time and at a sufficient temperature to disinfect the plastic conduit.

2. The method of claim 1, wherein:

in step (c), the sufficient temperature is at least 190° F. and the sufficient time is at least fifteen minutes.

3. The method of claim 2, wherein:

in step (c), the time does not exceed one hour.

4. The method of claim 1, wherein:

in step (c), the sufficient temperature is at least 220° F. and the sufficient time does not exceed one-half hour.

5. The method of claim 1, wherein:

in step (a), the fluid supply system includes polypropylene fittings connected to the cross-linked polyethylene conduit.

6. The method of claim 5, wherein:

in step (a), the fluid supply system includes straight sections of polypropylene conduit.

7. The method of claim 1, wherein:

in step (a), at least some of the cross-linked polyethylene plastic conduit is provided in lengths uncoiled from a coil of plastic conduit.

8. The method of claim 1, wherein:

in step (a) the cross-linked polyethylene plastic conduit is flexible conduit including at least one jointless segment at least 100 feet in length.

9. The method of claim 1, further comprising:
during step (c), bypassing at least one heat sensitive component of the system.

10. The method of claim 9, wherein the heat sensitive component is a reverse osmosis machine.

11. The method of claim 1, wherein:
in step (b), the hot water is ultrapure water of sufficient purity for use in a dialysis machine;
in step (a), the fluid supply system includes a heat exchanger having a first side through which the ultrapure water flows, and having a second side in heat exchange relationship with the first side; and
wherein the method further comprises:
providing a low pressure boiler for generating a hot second fluid; and
flowing the hot second fluid from the low pressure boiler through the second side of the heat exchanger to heat the ultrapure water flowing through the first side of the heat exchanger.

12. The method of claim 11, further comprising:
maintaining the pressure of the ultrapure water in the first side of the heat exchanger higher than the pressure of the second fluid in the second side of the heat exchanger, so that in the event of leaks in the heat exchanger, the ultrapure water in the first side of the heat exchanger cannot be contaminated by the second fluid.

13. The method of claim 1, wherein:
in step (a), the system includes a centralized bicarbonate mixing device for mixing bicarbonate solution for a plurality of dialysis machines in a clinic; and
the method further comprises flushing the bicarbonate solution from the system prior to step (c).

14. The method of claim 1, wherein:
in step (a), the system includes a storage tank in which the hot water is received, and from which it is circulated through the system by a circulation pump; and
the method further comprises:
prior to step (c), reducing the level of water in the storage tank to a minimum level required to prevent cavitation of the circulation pump; and
after step (c), disposing of the water to eliminate endotoxins from the system.

15. A method of heat disinfecting a fluid supply system for a dialysis clinic, comprising:
(a) providing a fluid supply system to the clinic including plastic conduit and a heat exchanger;
(b) providing a low pressure boiler for generating hot water;
(c) flowing hot water from the low pressure boiler through a dirty side of the heat exchanger while flowing fluid from the fluid supply system through a clean side of the heat exchanger to heat the fluid in the fluid supply system; and
(d) flowing the heated fluid through the fluid supply system for a sufficient time and at a sufficient temperature to disinfect the plastic conduit.

16. The method of claim 15, further comprising:
maintaining the pressure of the fluid in the clean side of the heat exchanger higher than the pressure of water in the dirty side of the heat exchanger, so that in the event of leaks in the heat exchanger water will be prevented from flowing from the dirty side into the clean side of the heat exchanger.

17. The method of claim 16, wherein the fluid in the clean side of the heat exchanger is maintained at a pressure of at least 1 psig higher than the pressure of fluid in the dirty side of the heat exchanger.

18. The method of claim 15, wherein:
the heat exchanger is a plate and frame heat exchanger having stainless steel plates.

19. The method of claim 15, wherein:
the low pressure boiler provides hot water at temperatures of up to about 222° F., at pressures of no greater than about 3 psig.

20. The method of claim 15, wherein:
in step (d), the sufficient temperature is at least 190° F. and the sufficient time is up to one hour.

21. The method of claim 15, wherein:
in step (d), the sufficient temperature is at least 220° F. and the sufficient time is up to one-half hour.

22. The method of claim 15, wherein:
in step (a), the system includes a centralized bicarbonate mixing device for mixing bicarbonate solution for a plurality of dialysis machines in the clinic; and
the method further comprises flushing the bicarbonate solution from the system prior to step (c).

23. The method of claim 15, wherein:
in step (a), the system includes a storage tank in which the fluid from the fluid supply system is received, and from which it is circulated through the system;
prior to step (c), reducing the level of fluid in the storage tank to a level below a normal operating level of the system; and
after step (d), disposing of the fluid to eliminate endotoxins from the system.

24. The method of claim 15, further comprising:
during step (d), bypassing at least one heat sensitive component of the system.

25. A method of heat disinfecting a centralized bicarbonate fluid supply system for a dialysis clinic, comprising:
(a) providing the fluid supply system with plastic conduit, and with a centralized bicarbonate mixing device for supplying bicarbonate fluid to a plurality of dialysis machines in the clinic;
(b) flushing the bicarbonate fluid from the fluid supply system; and
(c) after step (b), flowing hot water through the plastic conduit and the centralized bicarbonate mixing device for a sufficient time and at a sufficient temperature to disinfect the plastic conduit and the centralized bicarbonate mixing device.

26. The method of claim 25, wherein:
in step (c), the sufficient time is at least 6 hours and the sufficient temperature is at least 190° F., so that substantially all endotoxins in the fluid supply system are destroyed.

27. The method of claim 26, further comprising:
after step (c), allowing the water in the fluid supply system to cool;
then mixing bicarbonate with the cooled water to make new bicarbonate fluid; and
providing the new bicarbonate fluid to the dialysis machines.

28. A method of heat disinfecting a fluid supply system for a dialysis clinic, comprising:
(a) providing the fluid supply system with a fluid storage tank, a system circulating pump which pumps fluid from the storage tank, and a plastic conduit, the fluid storage tank being filled with ultrapure water up to an operating level during operation;

(b) lowering the level of ultrapure water in the fluid storage tank to a level below the operating level of the system;

(c) after step (b), heating the ultrapure water and flowing the heated water through the plastic conduit and the fluid storage tank for a sufficient time and at a sufficient temperature to disinfect the plastic conduit; and (d) after step (c), disposing of the heated water to remove from the system endotoxins which have been killed during the disinfecting process but the organic material of which is still present in the heated water, whereby the lowering of the water level in step (b) reduces the volume of water which must be disposed of in step (d).

29. The method of claim 28, wherein:

in step (b), the level of ultrapure water in the fluid storage tank is lowered to a level of at least a minimum level sufficient to allow the circulating pump to circulate the ultrapure water through the fluid supply system without cavitating.

30. A fluid supply system for a dialysis clinic, comprising:

plastic conduits disposed in the fluid supply system and constructed of plastic materials capable of heat disinfection;

a heat exchanger permanently installed as a part of the fluid supply system, the heat exchanger having first and second sides in heat exchange relationship, the plastic conduits being in fluid communication with the first side of the heat exchanger;

a plurality of dialysis machines connected to the fluid supply system; and a low pressure boiler connected to the second side of the heat exchanger for supplying hot water to the second side of the heat exchanger to heat fluids flowing through the fluid supply system, so that the fluid supply system can be disinfected by heated fluid flowing through the first side of the heat exchanger.

31. The system of claim 30, wherein:

the heat exchanger is a plate and frame heat exchanger.

32. The system of claim 31, wherein:

the plates of the heat exchanger are constructed of stainless steel.

33. The system of claim 30, wherein:

a pressure in the first side of the heat exchanger is maintained higher than a pressure in the second side of the heat exchanger.

34. The system of claim 30, further comprising:

a circulation pump for circulating hot water from the low pressure boiler through the second side of the heat exchanger and back to the low pressure boiler.

35. The system of claim 30, wherein:

at least some of the plastic conduits are constructed from cross-linked polyethylene.

36. The system of claim 35, further comprising:

polypropylene fittings connected to the cross-linked polyethylene conduits.

37. The system of claim 36, wherein:

some of the plastic conduits are constructed from polypropylene.

38. The system of claim 35, wherein:

at least one of the cross-linked polyethylene plastic conduits includes a seamless length of at least one hundred feet.

39. The system of claim 30, further comprising a centralized bicarbonate mixing device.

40. The system of claim 30, wherein the plastic conduits include:

at least one jointless segment of relatively flexible cross linked polyethylene conduit;

at least one straight segment of relatively rigid polypropylene conduit; and at least one polypropylene fitting connected to the polypropylene conduit.

* * * * *